United States Patent [19]
Bajer

[11] 3,979,418
[45] Sept. 7, 1976

[54] SILOXY SUBSTITUTED ARYLMERCAPTANS

[75] Inventor: Francis J. Bajer, Depew, N.Y.

[73] Assignee: Hooker Chemicals & Plastics Corporation, Niagara Falls, N.Y.

[22] Filed: Nov. 20, 1975

[21] Appl. No.: 633,750

Related U.S. Application Data

[62] Division of Ser. No. 401,316, Sept. 27, 1973, Pat. No. 3,939,210.

[52] U.S. Cl. .................. 260/448.8 R; 260/609 F
[51] Int. Cl.² ....................................... C07F 7/18
[58] Field of Search ........................... 260/448.8 R

[56] References Cited
UNITED STATES PATENTS

| | | |
|---|---|---|
| 2,967,192 | 1/1961 | Kantor .................. 260/448.8 R X |
| 3,388,144 | 6/1968 | Musolf et al. ............. 260/448.8 R |
| 3,440,302 | 4/1969 | Speier et al. ............ 260/448.8 R X |
| 3,465,015 | 9/1969 | Speier .................... 260/448.8 R X |

Primary Examiner—Paul F. Shaver
Attorney, Agent, or Firm—Peter F. Casella; William J. Crossetta, Jr.

[57] ABSTRACT

Mercaptophenols are selectively oxyalkylated at the mercapto function by a two-step process comprising reacting the mercaptophenol with a silylating agent to form novel silylated mercaptophenol derivatives and thereafter oxyalkylating the phenolic mercapto function to the degree of oxyalkylation desired. Simple hydrolyzing of the resulting product breaks the silylation block forming a hydrolyzed oxyalkylated mercaptophenol.

3 Claims, No Drawings

SILOXY SUBSTITUTED ARYLMERCAPTANS

This is a division of application Ser. No. 401,316, filed Sept. 27, 1973, now U.S. Pat. No. 3,939,210.

BACKGROUND OF THE INVENTION

Organic polymer compositions have numerous valuable properties which permit them to be used in the manufacture of a myriad of products. It has been observed however, that such polymers, under conditions of elevated temperatures and/or mechanical working, particularly in the presence of oxygen, undergo molecular degradation resulting in the deterioration of physical properties. Hydrolyzed oxyalkylated mercaptophenols have become very important as additives to polymer systems acting to retard and in some cases significantly arrest this degradation. U.S. Pat. No. 3,218,291 discloses examples to the uses of such mercaptophenols in retarding the degradation of synthetic rubber compositions, attesting to the growing importance of new and simpler methods for the preparation of high yield and high purity hydrolyzed oxyalkylated mercaptophenols.

Heretofore, the selective oxyalkylation of mercaptophenols in high yields and high purity has not been attainable. In a standard oxyalkylation of mercaptophenols, reaction at the mercapto function is always accompanied by some reacting of the hydroxy function because of the closeness in reactivity rates of the active hydrogen in the OH and SH functions.

It is an object of this invention to provide a process for the selective oxyalkylation of the mercapto function of a mercaptophenol. It is another object of this invention to provide a process wherein the mercapto function of a mercatophenol may be oxyalkylated in high yields and to a high degree of purity. Another object is to prepare new silylated derivatives of mercaptophenol compounds which are useful as intermediates for the preparation of oxyalkylated mercaptophenols. It is still another object of this invention to provide a simple process for the selective oxyalkylation of the mercapto function of a mercaptophenol. It is a further object to provide a new process for the preparation of hydroxy oxyalkylated mercaptophenols. These and other objects will become more apparent from the following discussion.

SUMMARY OF THE INVENTION

In accordance with this invention, the mercapto function of a mercaptophenol is oxyalkylated by a two step process comprising reacting the mercaptophenol with a silylating agent and thereafter oxyalkylating the product thereof. The silylation of the mercaptophenol compound can be accomplished by directly reacting any of the myriad of commonly available silylating agents with a mercaptophenol at varying conditions. The reaction is exemplified in its simplest form by the sequence

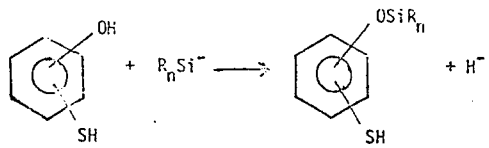

the mechanism of reaction is such that the acidic hydrogen proton of the hydroxy function preferentially reacts with the silyl group and is substituted therewith. The term "silyl group" is intended to mean the grouping $R_nSi^-$ where R is a monovalent hydrocarbon radical and n is from 0 to 3. Typical organo silicon compounds containing the silyl group and within the scope of this invention include the halo silanes of the generic formula $$R_nSi(Hal)_{4-n}$$

wherein R is an organic radical such as an alkyl group, alkenyl group, aryl group and the like; Hal is halogen; and n n a integer from 1 –3. A preferred halogen is chlorine. Further, organo silicon compounds of the generic formula

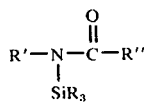

where R, R' and R'' are monovalent hyrocarbon radicals, R' is in addition hydrogen and the $SiR_3$ radical and R'' is in addition hydrogen and the

radical where Q is selected from the group consisting of hydrogen monovalent hydrocarbon radicals and the $-SiR_3$ group, are also effective silylating agents in the instant invention. Still further, silicon nitrogen compounds (hexaorgano disilazanes) of the formula $(R_3Si)_2$NH where R is a monovalent hydrocarbon radical are effective in the instant invention. U.S. Pat. Nos. 2,746,956; 3,043,798 and 3,397,220 disclose these and additional silylating agents which are operable in the instant invention. These and other silyl group containing compounds which selectively substitute the acidic hydrogen of the hydroxy function in the mercaptophenol are meant to be included within the scope of the instant invention.

The mercaptophenols which may be selectively oxyalkylated by this invention include any of the arylhyroxides such as phenol anethrol, plenatrol and their derivatives wherein a mercapto function is present. They may be saturated or unsaturated as monoatomic such as mercaptophenols, cresols, mesitols, durenols and thymols; diatomic such as mercaptodiphenols, -resorcinols, -orcinols, -dihydroxyxylols, -mesorcinols and -thymoquinols; triatomic such as mercapto-triphenols, -pyrogallols and -methyl pyrogallols; and poly atomic such as mercaptopolyphenols, -tetrahydroxy benzenes and -pentahydroxy benzenes. Accordingly, by mercaptophenol is meant compounds of the generic formula

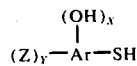

wherein Ar is a mono, di, tri or poly atomic phenol as hereinbefore described, each Z is independently hydrocarbon, halogen or hydrogen and the sum of X and Y is the total remaining substitutable positions of Ar.

The silylated derivatives formed by the method of the instant invention can be generically described as

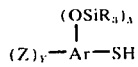

wherein Ar is a mono, di, tri or poly atomic phenol as hereinbefore described, each Z is independently hydrocarbon, halogen or hydrogen, R is a monovalent hydrocarbon radical and the sum of X and Y is the total remaining substitutable positions of Ar. The silylated derivatives preferred in the instant invention can be generically described as

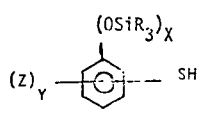

wherein R is a monovalent hydrocarbon radical, each Z is independently hydrocarbon, halogen or hydrogen and the sum of X and Y is 5.

The temperature of reaction of this invention may be widely varied, with reaction frequently occurring spontaneously upon mixing the reactants. Generally the temperatures may be varied from about ambient temperature to a temperature wherein the reactants or products are unstable (i.e., from about 0° centigrade to about 300° centigrade). Preferably the reaction temperature is within the range of about room temperature to about 120° centigrade and especially within the range of about 30° centigrade to about 100° centigrade.

The method of this invention is useful for modifying the mercapto function of mercaptophenols without effecting the hydroxy function. After silylation of the hydroxy function the mercapto function may be oxyalkylated by standard methods to the desired degree. The oxylaylated silylated material may then be readily hyrolyzed by subjecting to moisture under conditions so as to regenerate the hydroxy function as shown by the following schematic:

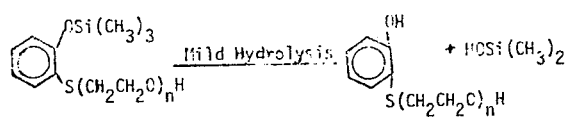

The by-product of the hydrolysis is an organic silicone compound which is readily separable from the phenol by standard separation techniques. The primary advantage of the present method lies in the fact that the condition for regeneration of the hydroxy function can be so mild that no problem occurs in concurrent hydrolysis of the mercapto function.

The following examples are illustrative only and should not be construed as limiting the invention which is properly delineated in the appended claims.

EXAMPLE 1

24.65 grams (0.154 mole) of hexamethyldisilazane was gradually added to 38.85 grams (0.308 moles) of orthomercaptophenol and a white solid was immediately formed. The solid mixture was then heated in an oil bath to a temperature of about 129°C. and maintained at that temperature until the evolution of gaseous $NH_3$ had ceased (approximately 2 hours). A 95% (by weight) yield of a light colored, clear, liquid product resulted, having a boiling point of 59-60 degrees centigrade at 0.5 millimeters of mercury, which, after cooling and vacuum distillation analyzed as follows:

|  | Theory | Found |
|---|---|---|
| % Carbon | 54.55 | 54.5 |
| % Hydrogen | 7.07 | 7.0 |
| % Sulfur | 16.15 | 15.92 |
| Mol. Wt. | 198 | 199 (in THF) |
| Refractive Index | — | $n_D^{25}$ 1.5238 |

NMR and IR analysis confirm the structure as consistent with silylated mercaptophenol of the formula:

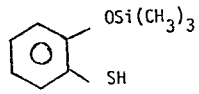

EXAMPLE 2

9.3 grams (0.10) of epichlorohydrin was rapidly added to a mixture containing 39.6 grams (0.20 mole) of ortho mercaptophenol-o-trimethyl silyl ether in 10 grams of triethylamine. A violent exotherm reaction ensued and the temperature rose to about 182°C. On cooling to room temperature a liquid solid slurry resulted. The slurry was extracted with ether yielding an 84% by weight yield of $(CH_3CH_2)_3N·HCl$. The ether filtrate was then stripped yielding 42 grams of a yellow colored liquid which on vacuum distillation analyzed as follows:

|  | Theory | Found |
|---|---|---|
| % Carbon | 55.60 | 55.30 |
| % Hydrogen | 7.13 | 6.85 |
| % Sulfur | 14.15 | 14.20 |
| Mol. Wt. | 453 | 436 (in MEK) |

NMR and IR analysis confirmed the structure:

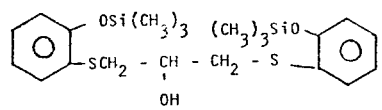

The above compound was mixed with aqueous ethanol in a 1:3 ratio and was heated to about 100° centigrade over a steam bath, resulting in the regeneration of the free phenolic function to yield a compound of the formula:

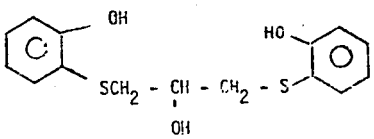

EXAMPLE 3

5.62 grams (0.0396 mole) of methyl iodide was gradually added to a mixture containing 7.85 grams (0.0396 moles) of orthomercaptophenol-o-trimethylsilylether dissolved in 4.0 grams (0.0396 moles) of triethylamine. Solids precipitated rapidly and temperature rose quickly to about 98°C. On cooling, 40 milliliters of ether was added and the solution filtered to remove the $(CH_3CH_2)_3N-$ salt. The filtrate was stripped of ether and vacuum distilled to yield a compound having the following analysis:

|              | Theory | Found       |
|--------------|--------|-------------|
| % Carbon     | 56.60  | 56.48       |
| % Hydrogen   | 7.60   | 7.45        |
| % Sulfur     | 15.12  | 15.00       |
| Mol. Wt.     | 212    | 218 (MEK)   |

NMR and IR analysis identified the structure as

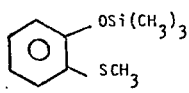

The above compound was mixed with aqueous ethanol in a 1:3 ratio and was heated to about 100°C. over a steam bath, resulting in the regeneration of the free phenolic function to yield a compound of the formula:

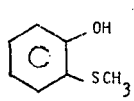

EXAMPLE 4

Ethylene oxide gas was slowly added by a sparger to a mixture containing 100 grams (0.51 moles) of ortho-mercaptophenol-O-trimethyl silyl ether and 0.5 grams of anhydrous $K_2CO_3$. A Nujol bubbling tower was used to monitor gas flow and provide a slight positive pressure of ethylene oxide equivalent to about 25 millimeters of mercury. The mixture was heated to a temperature of about 123°C. wherein a rapid uptake of ethylene oxide was observed together with a marked increase in exothermic reaction. Ethylene oxide additions continued for about 2 hours at a temperature of about 190°C. On cooling, the mixture was placed under a blanket of $N_2$. A portion of the reaction product was vacuum distilled yielding a clear white liquid having a boiling point of between about 96°C. to 98°C. at 0.3 millimeters of mercury. Analysis of the product gave the following:

|            | Theory | Found     |
|------------|--------|-----------|
| % Carbon   | 54.50  | 54.38     |
| % Hydrogen | 7.49   | 7.26      |
| % Sulfur   | 13.23  | 13.20     |
| Mol. Wt.   | 242    | 242(Avg.) |

NMR and IR analysis affirmed the structure as:

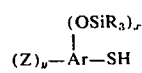

The above compound was mixed with aqueous ethanol in a 1:3 ratio and was heated to about 100°C. over a steam bath resulting in the regeneration of the free phenolic function to yield a compound of the formula:

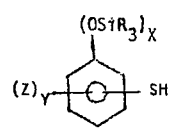

I claim:
1. A compound of the structure

$$(Z)_y-Ar\genfrac{}{}{0pt}{}{(OSiR_3)_x}{}-SH$$

wherein Ar is mono, di, tri or poly atomic aryl; each Z is independently selected from the group consisting of hyrocarbon, halogen or hydrogen; R is a monovalent hydrocarbon radical and the sum of X and Y is the total remaining substitutable positions of Ar.

2. A compound of claim 1 of the structure

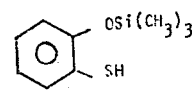

3. A compound of claim 2 of the structure

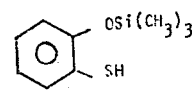

* * * * *